(12) United States Patent
Suguro et al.

(10) Patent No.: US 7,678,152 B2
(45) Date of Patent: *Mar. 16, 2010

(54) ARTIFICIAL KNEE JOINT

(75) Inventors: Toru Suguro, 1201-7, Chibadera-cho, Chuo-ku, Chiba-shi, Chiba (JP); Koichi Kuramoto, Okayama (JP); Keitaro Yamamoto, Okayama (JP)

(73) Assignees: Toru Suguro, Chiba (JP); Nakashima Propeller Co., Ltd., Okayama (JP)

( * ) Notice: Subject to any disclaimer, the term of this patent is extended or adjusted under 35 U.S.C. 154(b) by 657 days.

This patent is subject to a terminal disclaimer.

(21) Appl. No.: 11/081,990

(22) Filed: Mar. 16, 2005

(65) Prior Publication Data

US 2005/0209701 A1   Sep. 22, 2005

(30) Foreign Application Priority Data

Mar. 17, 2004 (JP) ............... 2004-075903

(51) Int. Cl.
A61F 2/38 (2006.01)
(52) U.S. Cl. ................ 623/20.27; 623/20.31
(58) Field of Classification Search ... 623/20.26–20.27, 623/20.32–20.34
See application file for complete search history.

(56) References Cited

U.S. PATENT DOCUMENTS

| | | | | |
|---|---|---|---|---|
| 4,261,064 A | * | 4/1981 | Helfet | 623/20.31 |
| 4,298,992 A | * | 11/1981 | Burstein et al. | 623/20.27 |
| 5,147,405 A | * | 9/1992 | Van Zile et al. | 623/20.27 |
| 5,192,328 A | * | 3/1993 | Winters | 623/20.31 |
| 5,549,686 A | * | 8/1996 | Johnson et al. | 623/20.27 |
| 5,702,458 A | * | 12/1997 | Burstein et al. | 623/20.31 |

(Continued)

FOREIGN PATENT DOCUMENTS

EP   0 123 016   10/1984

(Continued)

OTHER PUBLICATIONS

"Anatomy and Kinematics of the Knee Joint". Feb. 8, 2006. Duke Orthopaedics. Wheeless' Textbook of Orthopaedics. Online. http://www.wheelssonline.com/ortho/anatomy_and _kinemantics_ of _the_joint.*

*Primary Examiner*—Corrine M McDermott
*Assistant Examiner*—Christopher D Prone
(74) *Attorney, Agent, or Firm*—William L. Androlia; H. Henry Koda

(57) ABSTRACT

An artificial knee joint including a femoral component and a tibial component which are in relation of making relative rotation, in which the tibial component has a post that has an outwardly curving posterior surface and is disposed approximately in the longitudinal center between the articular surfaces so that the post is inside an intercondylar groove that is between the medial and lateral condyles and extends from the posterior end to the anterior end of the femoral component; and the femoral component has a cam that is disposed at the posterior portion of the intercondylar groove and comes into contact with the posterior surface of the post when the above-described rotation proceeds; and the post and the cam are shaped so that the femoral component is turned outwardly when the cam comes into contact with the post as a result of the rotation and as the rotation proceeds.

6 Claims, 6 Drawing Sheets

U.S. PATENT DOCUMENTS

| | | | | |
|---|---|---|---|---|
| 6,068,658 | A * | 5/2000 | Insall et al. | 623/20.3 |
| 6,168,629 | B1 * | 1/2001 | Timoteo | 623/20.27 |
| 6,235,060 | B1 * | 5/2001 | Kubein-Meesenburg et al. | 623/20.31 |
| 6,428,577 | B1 * | 8/2002 | Evans et al. | 623/20.29 |
| 6,475,241 | B2 * | 11/2002 | Pappas | 623/20.29 |
| 6,558,421 | B1 * | 5/2003 | Fell et al. | 623/14.12 |
| 6,582,469 | B1 * | 6/2003 | Tornier | 623/20.27 |
| 6,589,283 | B1 * | 7/2003 | Metzger et al. | 623/20.35 |
| 6,660,039 | B1 * | 12/2003 | Evans et al. | 623/20.29 |
| 6,972,039 | B2 * | 12/2005 | Metzger et al. | 623/20.29 |
| 7,066,963 | B2 * | 6/2006 | Naegerl | 623/20.32 |
| 2003/0153977 | A1 * | 8/2003 | Suguro et al. | 623/20.14 |
| 2004/0243244 | A1 * | 12/2004 | Otto et al. | 623/20.27 |

FOREIGN PATENT DOCUMENTS

| | | |
|---|---|---|
| EP | 1 336 395 | 8/2003 |
| EP | 1 374 805 | 1/2004 |
| FR | 2 701 387 | 8/1994 |
| FR | 2 702 651 | 9/1994 |
| FR | 2702651 A1 * | 9/1994 |
| JP | 11-313845 | 11/1999 |
| JP | 2003-116892 | 4/2003 |
| JP | 2003-230582 | 8/2003 |
| WO | WO 99/30649 | 6/1999 |

* cited by examiner

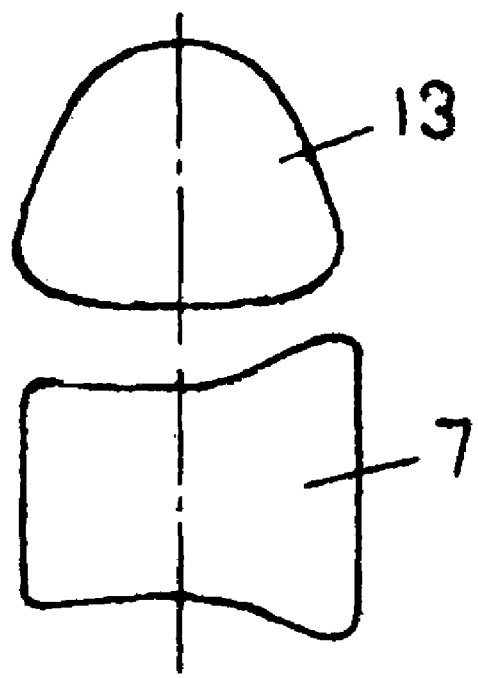 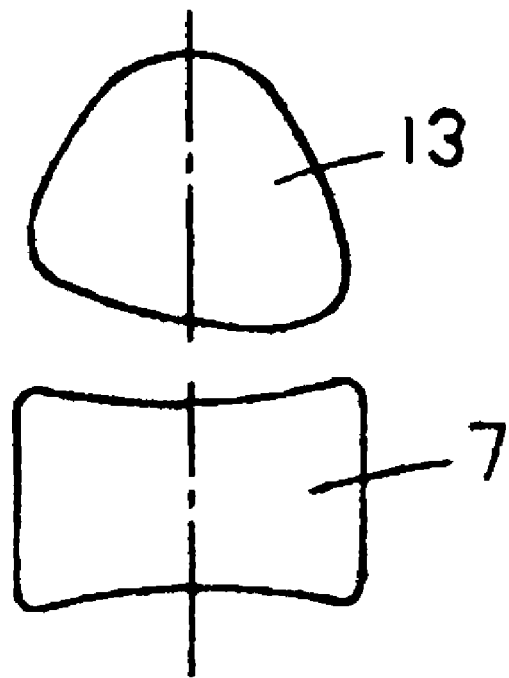
FIG. 7A  FIG. 7B

ARTIFICIAL KNEE JOINT

PRIORITY DATE

This application claims foreign priority to 2004-75903, filed Mar. 17, 2004.

BACKGROUND OF THE INVENTION

1. Technical Field

The present invention relates to an artificial knee joint to replace a knee joint.

2. Description of the Related Art

Artificial knee joint replacement is performed in cases in which the knee is afflicted by osteoarthritis, rheumatoid arthritis, or bone tumor, or is subjected to trauma and the like. This artificial knee is a combination of a femoral component that is to be attached to the distal end of the femur and has a medial condyle and lateral condyle and a tibial component that is to be attached to the proximal end of the tibia and has a medial articular surface and a lateral articular surface that support the medial condyle and lateral condyle, respectively. However, both of these condyles and articular surfaces must perform the same movements as a biological knee.

More specifically, when the knee is flexed, the femoral component and the tibial component do not dislocate by slipping to the front and back or right and left. The collateral ligaments and the anterior and posterior cruciate ligaments regulate this slipping to the front and back or left and right, but this ligament function is often destroyed or weakened and slipping readily occurs in patients that are suitable candidates for artificial knee replacement. Therefore, as disclosed in Japanese Patent Application Laid-Open (Kokai) Nos. 2003-116892 and 2003-230582, an artificial knee called a posterior-stabilized type is proposed in which a post is stood in approximately the longitudinal center between the articular surfaces of the tibial component and pushed into the intercondylar groove formed between the medial and lateral condyles of the femoral component, and a cam that will come into contact with the post with flexion at a certain angle is disposed at the posterior portion of the intercondylar groove to regulate slipping to the front and back or left and right.

On the other hand, the problem of rotation with the artificial knee cannot be forgotten. When the knee joint is flexed, the femur rotates laterally (the tibia rotates medially; these are called external rotation and internal rotation). This movement is insured in a biological knee by the joint line (abbreviated JL) connecting the lowest points of the medial condyle and lateral condyle in the medial-lateral (left-right) direction being lower on the medial condyle side (this is called inward inclination) than the SEA (flexion-extension center axis; the flexion center axis when standing, becomes horizontal). However, the artificial knee joint of the above-described example makes deep flexion possible by increasing the turning radius during the final stages of flexion and avoids concentration of stress by increasing the thickness of the cam periphery; therefore, particular attention is not given to the problem of rotation.

The inventors proposed inducing rotation more easily by inward inclination of the joint line of an artificial knee in Japanese Patent Application Laid-Open No. H11313845 and produced commensurate results. However, later research revealed that the PS-type artificial knee has other problems. More specifically, the post and the side surfaces of the intercondylar groove interfere with one another due to rotation during flexion. The post is worn by the interference and the powder from this abrasion invades bones and other tissues, causing them to dissolve and break down biologically. Therefore, this interference is avoided by making the post width much narrower than the width of the intercondylar groove. However, as a result, there is a reduction in strength of the post and the post may break. Moreover, the cam makes firm contact with the post at the end of flexion. If the post width is narrow at this time, there will be a reduction in contact surface area and surface pressure will rise to promote abrasion.

BRIEF SUMMARY OF THE INVENTION

The problems to be solved by the present invention is to provide smooth movement, readily induce rotation and make it possible to reduce abrasion and guarantee strength by skillfully devising the shape and placement of the post and cam taking into consideration the specific relationship between the post and intercondylar groove and the specific relationship between the condyles and the articular surfaces.

The above object is accomplished by a unique structure of the present invention for an artificial knee joint that includes:
  a femoral component to be attached to the distal end of a femur, and
  a tibial component to be attached to the proximal end of a tibia, the tibial component supporting the medial condyle and the lateral condyle of the femoral component by the medial articular surface and the lateral articular surface of the tibial component so that the femoral component and the tibial component are in relation of making rotation; and in the present invention,
  the tibial component is provided with a post that has an outwardly curving posterior surface, the post being disposed approximately in the longitudinal center between the two articular surfaces so that the post is inside the intercondylar groove which is formed between the medial condyle and the lateral condyle and extends from the posterior end to near the anterior end of the femoral component;
  the femoral component is provided with a cam that is disposed at the posterior portion of the intercondylar groove and comes into contact with the posterior surface of the post when the rotation proceeds; and
  the post and the cam are shaped so that the femoral component is turned outwardly with respect to the tibial component when the cam comes into contact with the post as a result of the rotation and as the rotation proceeds.

In the above structure, the cam is provided horizontally in the intercondylar groove and in a drum shape that is depressed in a center thereof, and the outer side diameter of the cam is larger than an inner side diameter thereof. In addition, the lateral articular surface side of the posterior surface of the post is set back from the medial auricular surface side thereof so that the center of the curvature is displaced outwardly. The lateral surface of the intercondylar groove is formed parallel to the center line of the fermoral component; the medial surface of the intercondylar groove gradually curves from the posterior end to the anterior end of the intercondylar groove and comes closer to the lateral condyle side beginning near an end of the cam; and the post is formed into substantially a triangular shape when viewed form above by reducing thickness of the side surfaces from the side surfaces toward the anterior surface. In addition, the curvature radius of the surface of the cam and the curvature radius of the posterior surface of the post are substantially the same; and the medial and lateral articular surfaces of the tibial component are concave in side view, and the posterior portion of the lateral articular surface is flat. Furthermore, the joint line that connects the lowest points of the contact surface between the medial condyle and the medial articular surface and the lowest points of the contact surface between the lateral condyle and the lateral articular surface in the medial-lateral vertical cross section is inclined medially at substantially the same angle over the entire inflexion-extension angle region.

With the above structure of the artificial knee joint of the present invention, rotation is induced as a result of the femur and the tibia flexing, that is, the femoral component and the tibial component turning. Thus, when rotation is spontaneously induced during flexion of the artificial knee joint, ligament balance is no different from that of a biological knee joint, smooth motion from the joint becomes possible, and it becomes possible to cope with the deep flexion actions unique to Japanese, including the formal way of sitting with one's legs folded and sitting cross-legged. The present invention provides specific shape and placement of the post and cam for inducing rotation. In the present invention, turning is induced from the early stages of rotation, and interference between the medial side surface of the intercondylar groove and the post at this time is prevented, abrasion is reduced, and smooth movement is realized. Furthermore, the cam rotates smoothly with respect to the post, contact surface area is increased, and abrasion is reduced. In addition, turning is induced over the entire angle of flexion.

BRIEF DESCRIPTION OF THE SEVERAL VIEWS OF THE DRAWINGS

FIGS. 7A and 7B are top views showing the relation of the post and cam of the artificial knee joint of the present invention.

DETAILED DESCRIPTION OF THE INVENTION

Figure 1:
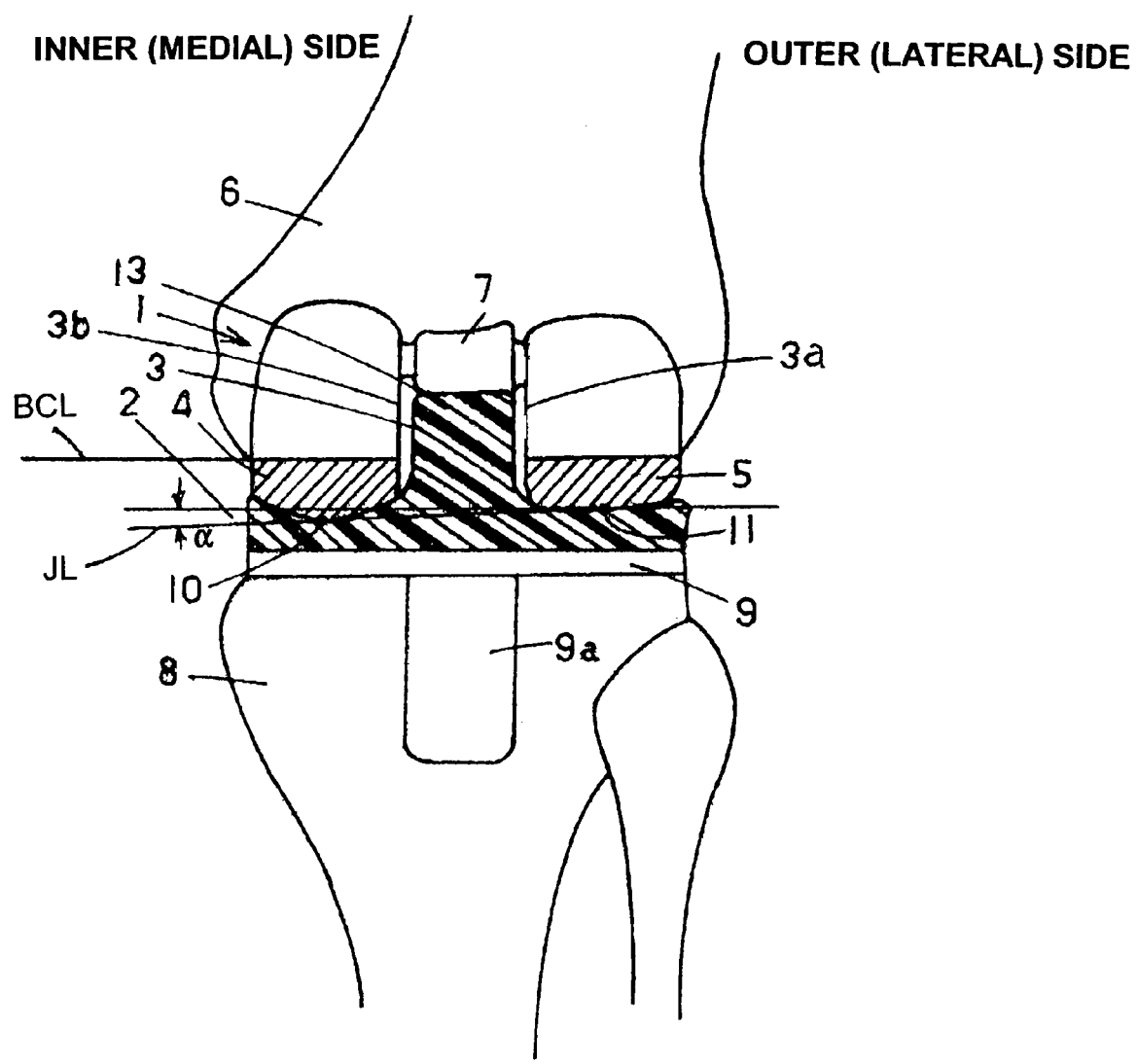
FIG. 1 is a rear view of the artificial knee joint according to one embodiment of the present invention.
Figure 2:
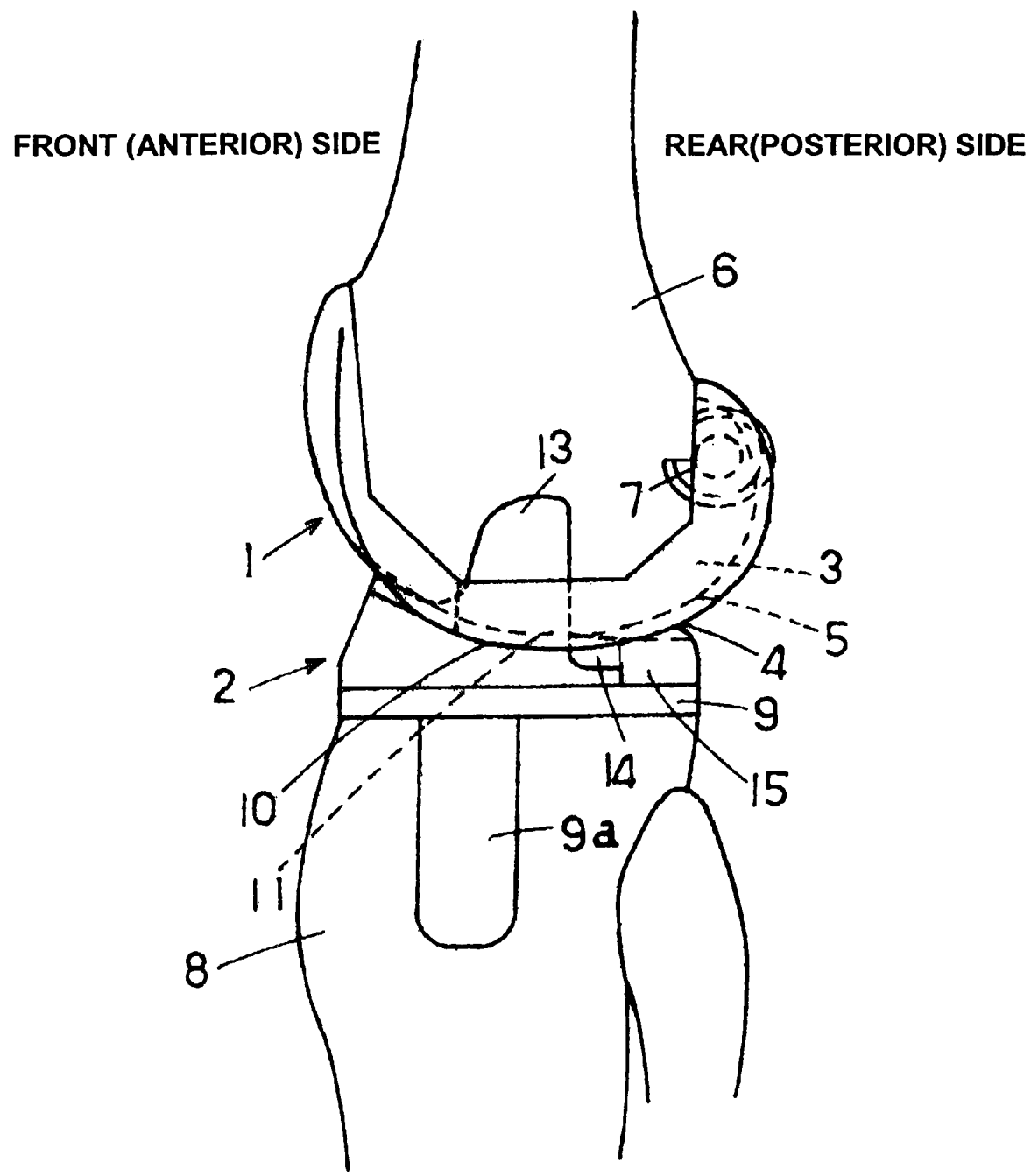
FIG. 2 is a partially cross-sectional side of the artificial knee joint of the present invention shown in FIG. 1.

The present invention will be described below in detail with reference to the preferred embodiments while referring to the drawings. FIG. 1 is a side view of an attached artificial knee joint in standing position as an example of the present invention. FIG. 2 is a cross section of a rear view of the same.

The artificial knee joint of the present invention is a combination of femoral component 1 and tibial component 2. The femoral component 1 is made from titanium alloy or another biocompatible metal; and it has inlet-shaped intercondylar groove 3 extending from the posterior end to near the anterior end disposed in the center and medial condyle 4 and lateral condyle 5 formed to substantially the shape of the letter C by the side view. The femoral component 1 is attached to the distal end of femur 6. The outline of medial condyle 4 and lateral condyle 5 is convex from the front to the back, and this convex shape is longitudinally contiguous in a stripe.

It should be noted that the position or direction, such as lateral, medial, front, back, left, and right, are cited in the description, and the reference here is the state where the right or the left knee (right knee in the shown example) is extended to the front.

Figure 4:
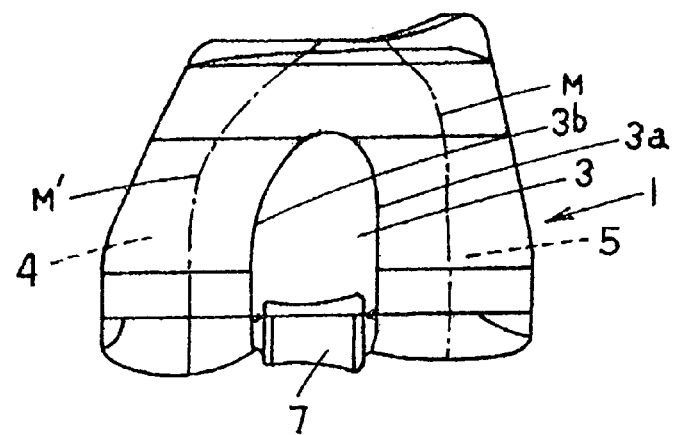
FIG. 4 is a top view of the femoral component of the artificial knee joint of the present invention.

FIG. 4 is a top view of femoral component 1. Cam 7 is provided horizontally over medial condyle 4 and lateral condyle 5 in the posterior portion of intercondylar groove 3 of the femoral component 1. This cam 7 has a drum shape with a depressed center; and in the shown example, the lateral condyle 5 side (or outer side) is formed to have a large diameter than the inner side. In order to improve fit with femur 6, the cam 7 is cut half way from the top along the line of the anterior surface of the posterior wall of femoral component 1. The cam 7 is made from the same material as femoral component 1. It can be formed as one unit with the femoral component or it can be made separately and then attached. Moreover, lateral surface 3a of intercondylar groove 3 extends parallel to the center line of intercondylar groove 3; and medial surface 3b extends, from the posterior end to the anterior end, in a gradual curve toward the lateral condyle 5 side beginning near the end of the cam 7 and connects the lateral surface 3a.

In contrast to this, the tibial component 2 is made from ultra-high-molecular-weight polyethylene or another medical resin, and it is attached to the proximal end of tibia 8. Thus, a combination of metal and resin is used to improve abrasion properties and provide for smoother movement. The tibial component 2 in this case is made from a biocompatible metal and is mounted on tibial base plate 9 with peg 9a that will be inserted into tibia 8. Medial articular surface 10 and lateral articular surface 11 that support medial condyle 4 and lateral condyle 5 of above-described femoral component 1, respectively, are formed in the top surface of tibial component 2 separated by low protrusion 12. These articular surfaces 10 and 11 are both concave following almost exactly the outline of medial condyle 4 and lateral condyle 5, and this concave shape extends longitudinally. In this case, the medial condyle 4 and lateral condyle 5 and the projected plane above or below medial articular surface 10 and lateral articular surface 11 are approximately the same size.

Figure 5:
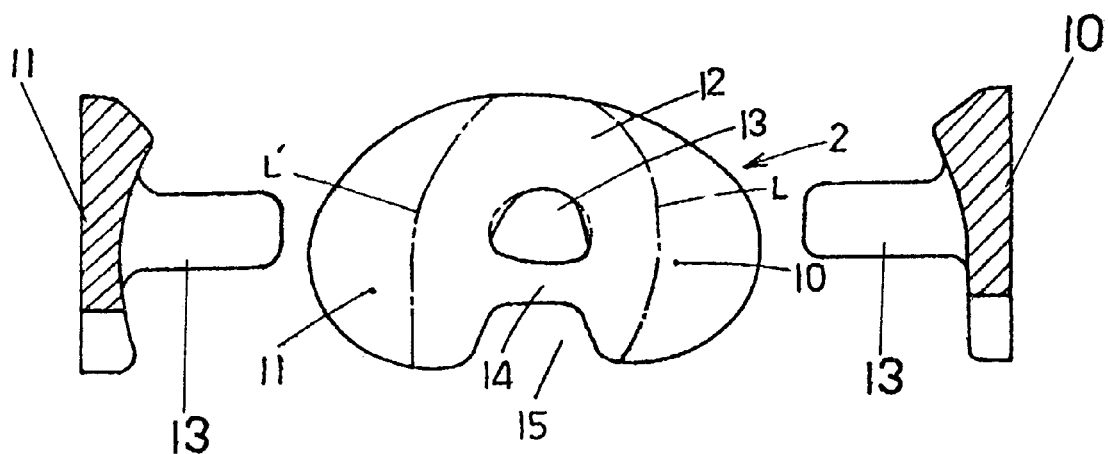
FIG. 5 is a top view of the tibial component of the artificial knee joint of the present invention with partially cross-sectional side views.

FIG. 5 is a top view of the tibial component 2, showing also both sides in cross section.

Both articular surfaces 10 and 11 are concave in the center. However, starting from the middle, the posterior portion of lateral articular surface 11 is flat and turns slightly back medially at the posterior end side thereof. Moreover, post 13 is provided to stand near approximately the center of medial and lateral articular surfaces 10 and 11. The post 13 is substantially circular at both the anterior surface and posterior surface when viewed from above, but the curvature radius of the posterior surface is larger and gradually curves outward. On the other hand, the post 13 has a substantially triangular shape that is formed by reducing thickness of the side surfaces from the side surfaces toward the anterior surface (the broken line is the outline when thickness is not reduced). In addition, the post 13 of the shown example is disposed slightly turned to the lateral condyle 5 side (twisted). The post 13 forms one unit made from the same material as the tibial component 2, but it can also be a separate unit and attached to the tibial component. In addition, concave part 14 is formed in the posterior portion of the post 13 depressed slightly more than either of articular surfaces 10 and 11, and the posterior portion of the concave part 14 is cut out to form a notched portion 15.

Femoral component 1 and tibial component 2 that form the above-described artificial knee joint rotate relatively with the flexion and extension of the knee. This is made possible by medial condyle 4 and lateral condyle 5 rotating as they roll and slide over the medial articular surface 10 and lateral articular surface 11 as the intercondylar groove 3 is guided by the post 13. The angle of rotation is −10 degrees to 150 degrees vertically. This is primarily rolling in the early stages and sliding in the final stages, but both movements are controlled by the collateral ligaments and other fibular ligaments, and also participate in the prevention of detachment (dislocation) of the medial condyle 4 and lateral condyle 5 from the medial articular surface 10 and lateral articular surface 11.

Figure 3:
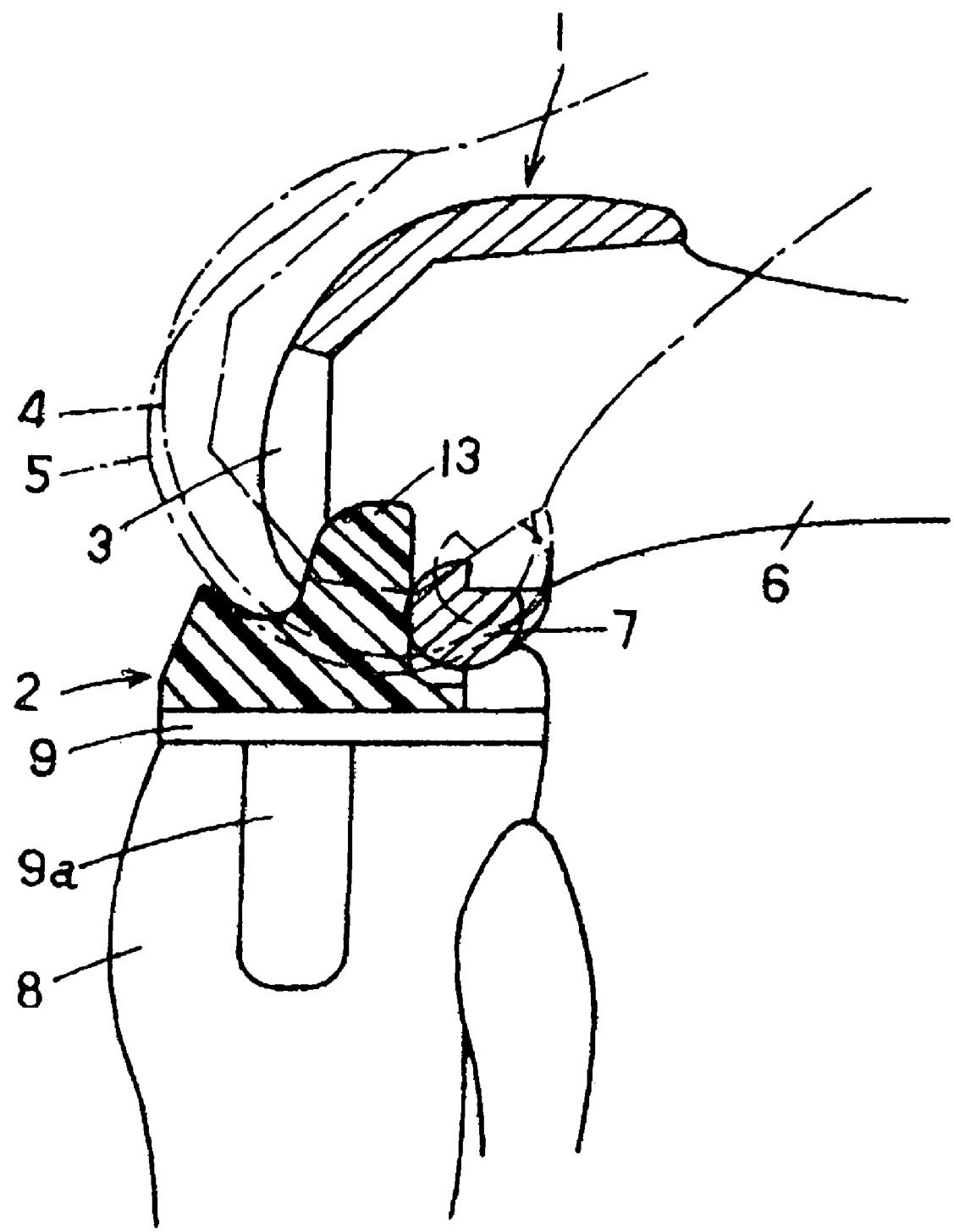
FIG. 3 is a side view showing the flexed state of the artificial knee joint of the present invention.

FIG. 3 is a side view showing the state where femoral component I and tibial component 2 rotate relatively with flexion of the knee. In a standing position with the knee extended (flexion angle of 0 degree), the cam 7 of the femoral component 1 is positioned away from the post 13 of the tibial component 2 (FIG. 1). The medial condyle 4 and lateral condyle 5 of the femoral component 1 roll and slide over the medial articular surface 10 and lateral articular surface 11 of the tibial component 2, and the cam 7 comes closer to the post 13 as the knee flexes.

With respect to the shape of above-described medial surface 3b of the condylar groove 3, it induces smooth lateral (outward) rotation, that is, external rotation, of the femoral component 1 from the early stages of flexion, and at the same time reducing thickness of the side surfaces of post 13 will result in avoiding interference between the medial surface 3b and post 13 for smooth movement and reducing abrasion. During flexion of the knee joint, the contact surface between the medial condyle and articular surface stays in place, and the contact surface between the lateral condyle and articular surface moves back from the femur. In other words, a rotational motion is made centered around the medial condyle 4 side and rotation is therefore smoothly induced. Consequently, retention of this contact surface is guaranteed by making the medial articular surface 10 that supports the medial condyle 4 concave with a depressed center, and backward movement of lateral condyle 5 is facilitated by making the posterior portion of the lateral articular surface 11 that supports the lateral condyle 5 flat. When the angle of flexion becomes approximately 70 degrees, the cam 7 touches or comes into contact with the post 13, so that thereafter they make rotation up to the maximum inflexion angle is accomplished as the components are regulated and guided by the cam and the post. In this case, the posterior portion of the lateral articular surface 11 turns back medially, and femoral component 1 rotates outwardly further at the end of flexion (tibial component 2 turns medially). In other words, a type of toe-in motion is made and helps to realize the same type of movement as a biological knee joint.

Figure 6:
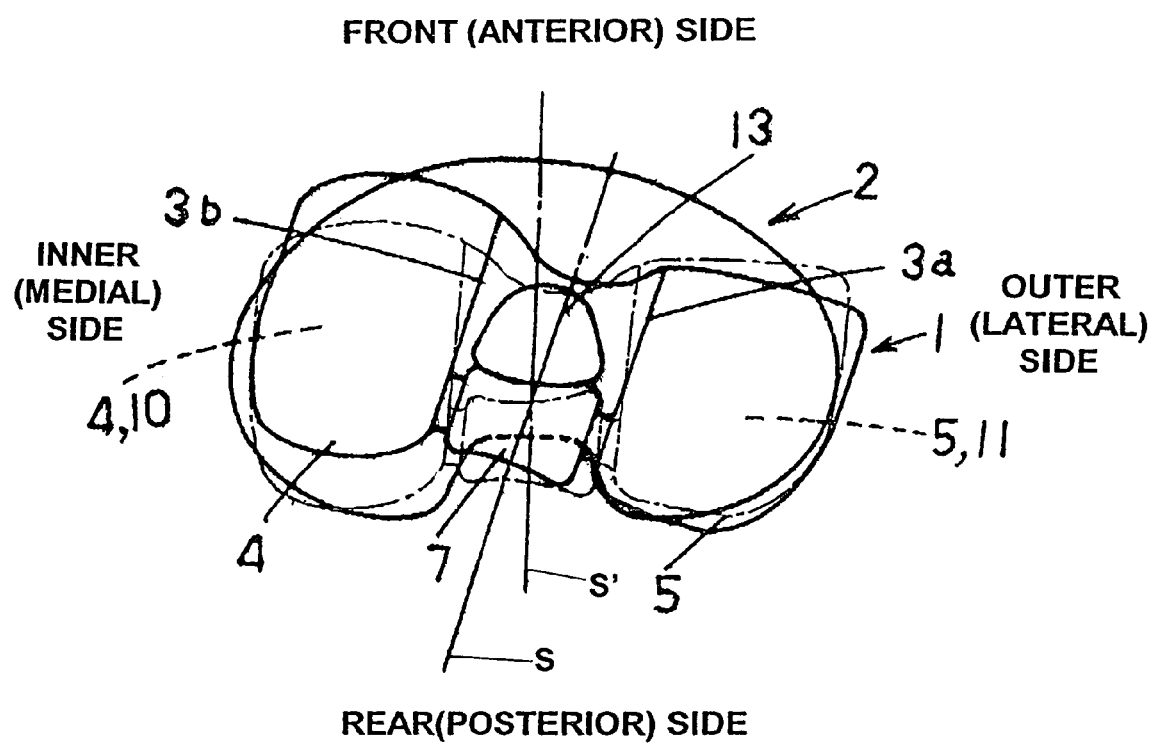
FIG. 6 is a top view showing the correlation between the tibial component and femoral component of the artificial knee joint of the present invention when the knee is flexed.

FIG. 6 is a top view of an artificial knee joint showing the above-described state. In this case, the cam 7 has the shape of a drum wherein the lateral condyle 5 side (outer side) has a large diameter than the inner side, and the post 13 has the shape in which the surface that comes into contact with the post 13, or its posterior surface, is a gradually outwardly curving surface that is disposed to be turned slightly to the lateral condyle 5 side. Therefore, there is further external turning of cam 7 or femoral component 1, when it comes into contact with the post 13. Although not illustrated, by way of increasing the outer diameter of cam 7 during the final stage of its rotation, it is possible to gradually increase the degree of the outward (lateral) turning of the femoral component 1. Making the curvature radius of the drum shape of cam 7 approximately the same as the curvature radius of the posterior surface of post 13 in this case will increase the contact surface area and thereby realize smooth movement as well as help to reduce wear.

The above description is made for an example in which the cam 7 is formed so that it has a larger diameter on the lateral condyle 5 side and the post 13 is disposed turned slightly toward the lateral condyle 5 side. This is a preferred embodiment for turning the femoral component 1 outwardly, but external turning of the lateral condyle 5 is not limited to this example and can be by other designs. Also, shown in FIG. 6 is the tibial centerline S' and the temoral centerline S.

FIGS. 7A and 7B show the relationship between the cam 7 and post 13 in which the outward (or lateral) turning is made possible. As long as the diameter of cam 7 is larger on the lateral condyle 5 side (or the outer side), the post 13 can face the cam 7 square as shown in FIG. 7A. However, even if the cam 7 is symmetric in terms of right and left diameter, the lateral articular surface 11 side at the posterior surface of the post 13 should be set back from the medial articular surface 10 side, that is, the center of the curvature (or radius) can be displaced outward as shown in FIG. 7B.

Furthermore, in the femoral component 1 of the artificial knee joint of the shown embodiment of the present invention, the medial condyle 4 is substantially uniformly thicker over the entire flexion-extension angle region than the lateral condyle 5. Accordingly, the medial articular surface 10 of the tibial component 2 is substantially uniformly thinner over the entire flexion-extension angel region than the lateral articular surface 11. More specifically, the outside periphery of the medial condyle 4 and lateral condyle 5 and the medial articular surface 10 and lateral articular surface 11 is graded such that the balance between tension and relaxation of the respective collateral ligaments will not be destroyed; and joint line L connecting the lowest points on the contact surface between medial articular surface 10 and lateral contact surface 11 that receive medial condyle 4 and lateral condyle 5, respectively, is set to be lower in the medial direction, that is, is inclined inward, in the medial-lateral vertical cross section.

The above graded structure can be made when the femoral component 1 and tibial component 2 are produced; therefore, during surgery fracture line BCL of the femur is made parallel to the SEA, and the fracture line of the tibia is made parallel to the BCL and perpendicular to the machine axis, that is, the center axis of the tibia. Consequently, surgical problems are not encountered with the artificial knee joint of the present invention.

The above design is made because it meets the structure of a biological knee joint; and by way of making the artificial knee the same as the biological knee, the balance between tension and relaxation of the collateral ligament is not damaged, and knee function (flexion-extension) after replacement will be the same as that of a biological knee. The inward inclination angle α of joint line JL in this case is the same as that of a biological knee joint at 1 to 10 degrees, preferably 2 to 5 degrees. Other than this, in the shown example, the curvature radius of the convex surface of the medial condyle 4 is smaller than that of the lateral condyle 5; accordingly, the curvature radius of the concave surface of the medial articular surface 10 is smaller than that of the lateral articular surface 11.

Furthermore, in the shown example, as seen from FIG. 4, the maximum thickness line M obtained by longitudinally connecting the points of maximum thickness of the medial condyle 4 turns outward as it moves forward and the distance from maximum radial line M' obtained by longitudinally connecting the points of maximum thickness of the lateral condyle 5 (becomes substantially straight longitudinally) becomes narrower (as a result, as seen from FIG. 5, lines L and L' corresponding to these lines of FIG. 4 are also formed by medial and lateral articular surfaces 10 and 11). In other words, a so-called toe-in design is created as shown in FIGS. 4 and 5. As a result, turning of the tibia 8 is further induced when the knee is flexed.

As seen from the above, according to the artificial knee joint of the present invention, with the above-described unique shape and placement of the cam 7 and post 13, and with the above-described unique shape of the intercondylar groove 3 and both articular surfaces 10 and 11, it is possible to induce rotation during flexion without destroying the balance between tension and relaxation of the ligaments, particularly the collateral ligaments. Consequently, movement similar to that of a biological knee joint is made without any discomfort, and there is no reduction in function even a part of the ligaments is cut during surgery; and surgical time and other stress to the patient is reduced. Furthermore, when the joint line JL is made inclined inward, it is possible to realize deep flexion of 130 degrees or more because rotation is more easily induced during flexion and extension o the knee.

The invention claimed is:

1. An artificial knee joint comprising:
a femoral component adapted to be attached to a distal end of a femur, and
a tibial component adapted to be attached to a proximal end of a tibia, said tibial component supporting a medial condyle and a lateral condyle of said femoral component by a medial articular surface and a lateral articular surface of said tibial component so that said femoral component and said tibial component are in relation of making rotation; wherein
said tibial component is provided with a post that has an outwardly curving posterior surface in such a manner that a lateral articular surface side of said posterior surface of said post is set back from a medial auricular surface side thereof so that a center of said curving posterior surface is turned outwardly to said lateral condyle side and in such a manner that said post is formed into substantially a triangular shape when viewed form above by reducing a thickness of side surfaces from the side surfaces toward an anterior surface, said post being disposed approximately in a longitudinal center between said two articular surfaces so that said post is inside an intercondylar groove which is formed between said medial condyle and said lateral condyle and said intercondylar groove extends from a posterior end to near an anterior end of said femoral component, said intercondylar groove being comprised of a lateral surface and a medial surface so that said lateral surface is parallel to a longitudinal direction of said tibial component, and said medial surface is parallel to the longitudinal direction from posterior end to substantially a center in the longitudinal direction and then from the center towards the anterior end gradually curves and comes closer to said lateral condyle side such that the intercondylar groove extends towards the lateral condyle side;
said femoral component is provided with a cam that is disposed at a posterior portion of said intercondylar groove and a surface of said cam in a lengthwise direction comes into direct contact with said curving posterior surface of said post when said rotation proceeds, said cam being-provided horizontally in said intercondylar groove and in a drum shape with an outer lateral side diameter of said cam being larger than an inner medial side diameter thereof; and
said post and said cam are provided so that said femoral component is turned outwardly with respect to said tibial component when said rotation proceeds.

2. The artificial knee joint according to claim 1, wherein said medial articular surface that supports the medial condyle is in a concave shape having a depressed center, and a posterior portion of said lateral articular surface that supports the lateral condyle is flat.

3. The artificial knee joint according to claim 1 or 2, wherein a curvature radius of a surface of said cam and a curvature radius of a posterior surface of said post are substantially the same.

4. The artificial knee joint according to claim 3, wherein a joint line that connects the lowest points of a contact surface between said medial condyle and said medial articular surface and the lowest points of a contact surface between said lateral condyle and said lateral articular surface in a medial-lateral vertical cross section is inclined medially at substantially the same angle over an entire inflexion-extension angle region, rotation and as the rotation proceeds.

5. The artificial knee joint according to claim 1 or 2, wherein a joint line that connects the lowest points of a contact surface between said medial condyle and said medial articular surface and the lowest points of a contact surface between said lateral condyle and said lateral articular surface in a medial-lateral vertical cross section is inclined medially at substantially the same angle over an entire inflexion-extension angle region, rotation and as the rotation proceeds.

6. The artificial knee joint according to claim 1, wherein said drum shaped cam has a diameter which increases gradually from an inner medial side to an outer lateral side thereof.

* * * * *